United States Patent
Li et al.

(10) Patent No.: US 12,347,532 B2
(45) Date of Patent: Jul. 1, 2025

(54) BOLTZMANN-BASED METHOD FOR SIMULATING CVI DENSIFICATION PROCESS OF COMPOSITE MATERIAL

(71) Applicants: SHAOXING RESEARCH INSTITUTE OF SHANGHAI UNIVERSITY, Zhejiang (CN); SHANGHAI UNIVERSITY, Shanghai (CN)

(72) Inventors: Aijun Li, Zhejiang (CN); Dan Zhang, Zhejiang (CN); Jingchao Yuan, Zhejiang (CN); Meihua Shi, Zhejiang (CN)

(73) Assignees: SHAOXING RESEARCH INSTITUTE OF SHANGHAI UNIVERSITY, Zhejiang (CN); SHANGHAI UNIVERSITY, Shanghai (CN)

( * ) Notice: Subject to any disclaimer, the term of this patent is extended or adjusted under 35 U.S.C. 154(b) by 642 days.

(21) Appl. No.: 17/291,742

(22) PCT Filed: Jun. 4, 2020

(86) PCT No.: PCT/CN2020/094447
§ 371 (c)(1),
(2) Date: May 6, 2021

(87) PCT Pub. No.: WO2020/244597
PCT Pub. Date: Dec. 10, 2020

(65) Prior Publication Data
US 2022/0130497 A1  Apr. 28, 2022

(30) Foreign Application Priority Data
Jun. 5, 2019 (CN) .......................... 201910487883.6

(51) Int. Cl.
*G16C 60/00* (2019.01)
*G06F 30/10* (2020.01)
*G06F 30/25* (2020.01)
*G06F 113/26* (2020.01)
*G16C 20/10* (2019.01)

(52) U.S. Cl.
CPC ............. *G16C 60/00* (2019.02); *G06F 30/10* (2020.01); *G06F 30/25* (2020.01); *G06F 2113/26* (2020.01)

(58) Field of Classification Search
CPC ......... G16C 60/00; G16C 20/10; G06F 30/10; G06F 30/25; G06F 2113/26; G06F 30/20
See application file for complete search history.

(56) References Cited

U.S. PATENT DOCUMENTS

2013/0116997 A1* 5/2013 Sun .................. G06F 30/15
703/9

FOREIGN PATENT DOCUMENTS

| CN | 107451307 A | 12/2017 |
|----|-------------|---------|
| CN | 108267390 A | 7/2018 |
| CN | 109684699 A | 4/2019 |
| CN | 110263394 A | 9/2019 |
| EP | 3046892 B1  | 3/2020  |

OTHER PUBLICATIONS

Ros W et al (2011) Simulation of chemical vapor infiltration and deposition based on 3D images: a local scale approach. Chemical Vapor Deposition 17.10-12: 312-320. (Year: 2011).*
Guan K et al (2013) Prediction of permeability for chemical vapor infiltration. Journal of the American Ceramic Society 96.8 2445-2453. (Year: 2013).*
Fu A (2019) Investigation of fluid wicking behavior in microchannels and porous media by direct numerical simulation (Order No. 28186341). Available from ProQuest Dissertations & Theses Global. (2456856514). (Year: 2019).*
Tang GH et al. (2007) Simulating two-and three-dimensional microflows by the lattice Boltzmann method with kinetic boundary conditions. Int J of Modern Physics C, 18(5): 805-817. (Year: 2007).*
International Search Report of International Searching Authority for PCT/CN2020/094447, ISA/CN, Beijing, China, Dated: Aug. 24, 2021.
Written Opinion of International Searching Authority for PCT/CN2020/094447, ISA/CN, Beijing, China Dated: Aug. 24, 2020.

* cited by examiner

*Primary Examiner* — Olivia M. Wise
*Assistant Examiner* — Vy Rossi
(74) *Attorney, Agent, or Firm* — M&B IP Analysts, LLC

(57) ABSTRACT

A Boltzmann-based method for simulating a CVI densification process of a composite material is provided. Phase space occupancy is provided in the method, such that a geometrical model can be presented by using the concept of a matrix, and components of a space are distinguished; and a phase space occupancy matrix can directly participate in operation, which is equivalent to a natural division of grids and boundaries, and the boundaries are presented by a phase parameter, which is a natural capturing process. Flow field calculation of the method uses virtual time step calculation, such that a boundary condition can be written in a unified form, thereby improving the programmability.

3 Claims, 4 Drawing Sheets

BOLTZMANN-BASED METHOD FOR SIMULATING CVI DENSIFICATION PROCESS OF COMPOSITE MATERIAL

CROSS-REFERENCE TO RELATED APPLICATIONS

This application claims priority under 35 U.S.C 371 to the International Application No.: PCT/CN2020/094447, filed on Jun. 4, 2020, and to the Chinese Patent Application No.: 201910487883.6, filed on Jun. 5, 2019, the contents of which are hereby incorporated by reference.

TECHNICAL FIELD

The present disclosure relates to the field of Chemical Vapor Infiltration (CVI) densification, in particular to a Boltzmann-based method for simulating a CVI densification process of a composite material.

BACKGROUND

Chemical Vapor Infiltration (CVI) is a special Chemical Vapor Deposition (CVD) process, which is characterized by allowing gaseous reactants to penetrate (or infiltrate) a porous structure (preform), depositing on the surface of the structure, accumulating gradually to achieve densification, and finally forming a composite material consisted of a preform and a matrix. The chemical reaction and thermodynamics of CVI are the same as those of CVD, but the kinetics are different, because the reaction gas must diffuse inward through the porous structure, while the by-product gas must diffuse outward. Therefore, the conventional CVI process usually needs to be carried out in the low temperature region controlled by kinetics to obtain the maximum penetration depth and product density, which has the characteristics of a long cycle. Many factors will affect the process at the same time. Using computer simulation technology and establishing a reasonable mathematical model is helpful to deepen the understanding of the CVI process mechanism, shorten the optimization cycle of process parameters, and carry out some experiments that are difficult to carry out due to economic reasons or experimental conditions, which is of great positive significance to the research of the CVI process.

The essence of densification process is a continuous growth process of a matrix on the interface, involving a series of mechanisms such as heat transfer, mass transfer, gaseous reaction, surface adsorption, surface reaction and so on. At present, the commonly used interface tracking methods include an adaptive grid method, a phase field model, level set, smoothed particle hydrodynamics (SPH) method and so on. However, the level set method can only be used for a two-phase interface. The phase field method introduces one or more continuously changing order parameters, which is complicated in calculation, high in academic background and high in calculation cost. The adaptive grid method is a Computational Fluid Dynamics (CFD) method, which limits the change range of the grid and the combination with chemical reaction. The smoothed particle hydrodynamics method needs microscopic attributes such as particle attributes, and it is difficult to deal with the particle transformation caused by chemical reaction. Because of the complexity and specialty of these methods, they have not been applied to the simulation of the CVI process and are difficult to be applied to practical engineering.

SUMMARY

To solve the problems existing in the prior art, the present disclosure provides a Boltzmann-based method for simulating a CVI densification process of a composite material.

To achieve the above purpose, the present disclosure provides the following scheme.

A Boltzmann-based method for simulating a CVI densification process of a composite material is provided, comprising the steps of:
1) geometric modelling: wherein a three-dimensional model of a preform is made on a computer, a three-dimensional matrix is produced by scanning pixels one by one, the component number of each pixel is recorded at the same time, and the component information of the pixel is stored in a matrix form in one-to-one correspondence with the spatial position, which is referred to as a component matrix;
2) assignment of a phase component: wherein according to the spatial distribution relationship recorded by the component matrix and the studied attribute relationship, the required attributes are extracted to establish a matrix, perform normalization processing to obtain a phase matrix, and count the volume occupancy of a certain phase in the spatial position from the phase matrix, that is, the ratio of the amount of substances in the phase component to the amount of all substances that are capable of being accommodated in the space;
3) grid division: wherein the phase component matrix is re-divided according to actual needs, an independent phase component matrix is established for different phase components, and all the phase component matrices are superimposed into a real geometric model;
4) assignment of material attributes: wherein material attributes are assigned according to the re-divided grid phase matrix, and the basic way is one-to-one multiplication of a phase matrix and a material attribute matrix;
5) boundary setting: wherein boundary conditions are set according to different actual conditions;
6) flow field calculation: wherein the Lattice Boltzmann Method (LBM) is used to calculate the gas-phase flow field, and the core is divided into two sub-processes: a) taking a virtual time step so that all particles move without restriction on a set of virtual grids; b) then, taking a modified time step, releasing the particles entering the boundary according to the boundary conditions described by each phase matrix, and modifying the flow field;
7) chemical reaction calculation: wherein the chemical reaction is calculated by a phase transformation algorithm, which is to scale the chemical reaction according to the actual reaction relationship after calculation under specified conditions, and add and subtract on the basis of the phase matrix;
8) circulating the steps 6) and 7) until the reaction ends;
9) processing results: wherein the calculated phase matrix is output and count, and is compared with the original matrix to obtain the relevant information after CVI densification.

Preferably, the boundary conditions in step 5) can be periodic boundary conditions, fixed boundaries, adiabatic boundaries or mapping boundaries; in general, the inlet and the outlet of gas are fixed boundaries, and the contact boundary between a preform and a CVI furnace wall is an adiabatic boundary; for example, the periodic boundary condition is used for a small part of the whole large preform.

Preferably, the three-dimensional model of the preform is drawn by software Computer-Aided Design (CAD), Solid-Works® or Geodict®.

Compared with the prior art, the present disclosure has the following technical effects.
1) Phase space occupancy is provided in the present disclosure, such that a geometrical model can be presented by using the concept of a matrix, and components of a space are distinguished; and a phase space occupancy matrix can directly participate in operation, which is equivalent to a natural division of grids and boundaries, and the boundaries are presented by a phase parameter, which is a natural capturing process.
2) Flow field calculation of the present disclosure uses virtual time step calculation, such that a boundary condition can be written in a unified form, thereby improving the programmability.

BRIEF DESCRIPTION OF THE DRAWINGS

The present disclosure will be further explained with reference to the accompanying drawings.

DETAILED DESCRIPTION

Figure 1:
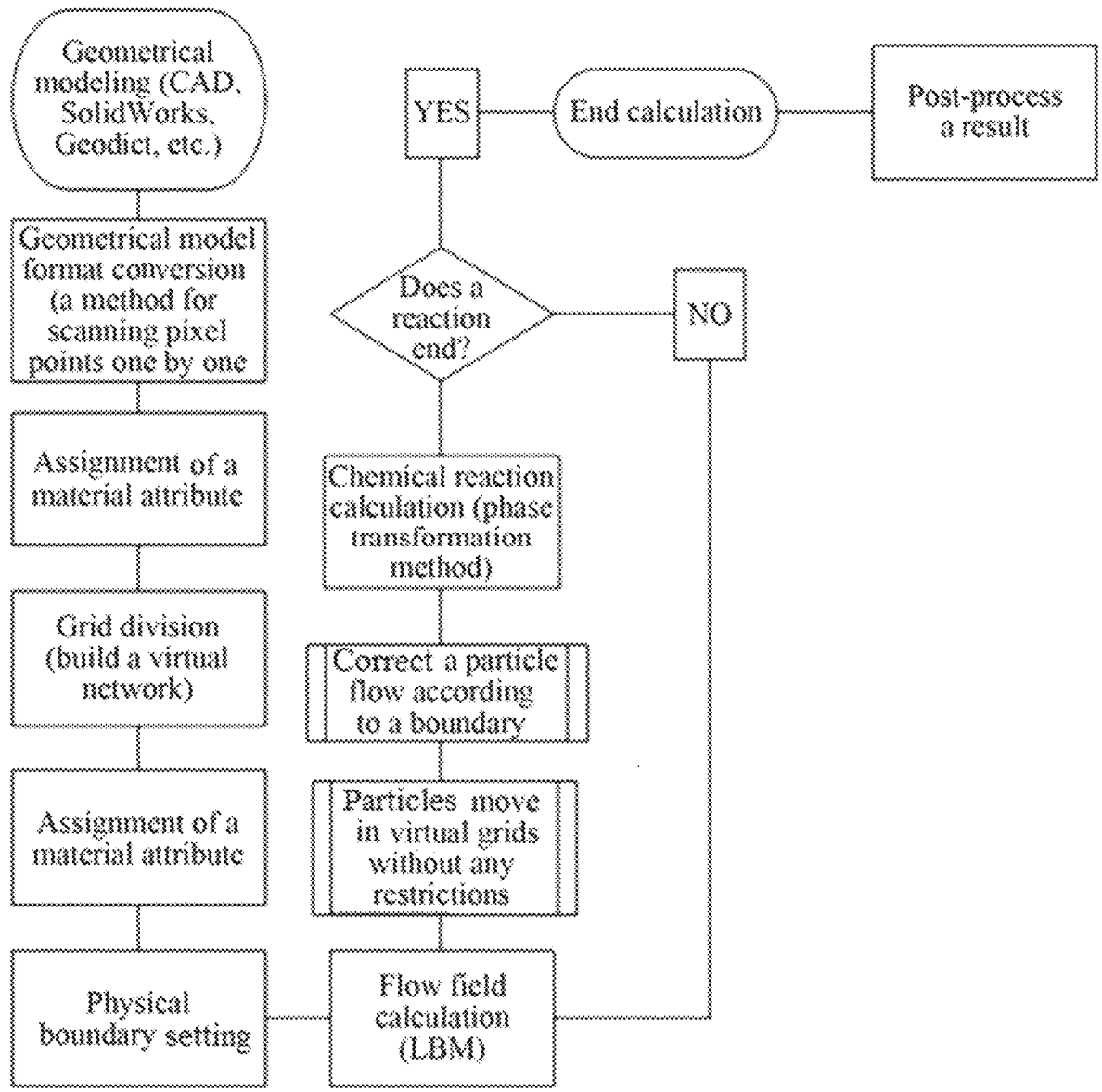
FIG. 1 is a flow chart of a Boltzmann-based method for simulating a CVI densification process of a composite material according to an embodiment of the present disclosure.
Figure 2:
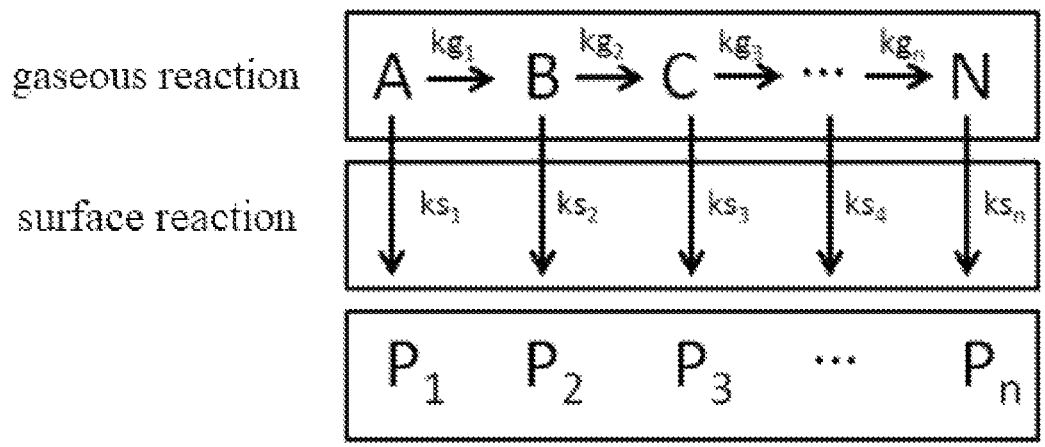
FIG. 2 is a schematic diagram of the parallel chain reaction according to the present disclosure (A, B, C and N are gaseous reactants and intermediate products; P is the target product)

FIG. 1 is a flow chart of a Boltzmann-based method for simulating a CVI densification process of a composite material according to an embodiment of the present disclosure. All gaseous reactants have the ability to contact and react with the surface of the preform to form the target product, which is controlled by the surface reaction constant ks (if ks=0, there is no reaction ability). In addition, the gaseous products will also undergo gaseous reaction to generate intermediate products, and the reaction is determined by the gaseous reaction constant kg. The whole reaction path becomes chain reaction. FIG. 2 is a schematic diagram of the parallel chain reaction according to the present disclosure (A, B, C and N are gaseous reactants and intermediate products; P is the target product).

As shown in FIG. 1, a Boltzmann-based method for simulating a CVI densification process of a composite material comprising the steps of:
1) geometric modelling: wherein a three-dimensional model of a preform is made on a computer, a three-dimensional matrix is produced by scanning pixels one by one, the component number of each pixel is recorded at the same time, and the component information of the pixel is stored in a matrix form in one-to-one correspondence with the spatial position, which is referred to as a component matrix; the three-dimensional model of the preform is drawn by software CAD, SolidWorks® or Geodict®;
2) assignment of a phase component: wherein according to the spatial distribution relationship recorded by the component matrix and the studied attribute relationship, the required attributes are extracted to establish a matrix, perform normalization processing to obtain a phase matrix, and count the volume occupancy of a certain phase in the spatial position from the phase matrix, that is, the ratio of the amount of substances in the phase component to the amount of all substances that are capable of being accommodated in the space;
3) grid division: wherein the phase component matrix is re-divided according to actual needs, an independent phase component matrix is established for different phase components, and all the phase component matrices are superimposed into a real geometric model;
4) assignment of material attributes: wherein material attributes are assigned according to the re-divided grid phase matrix, and the basic way is one-to-one multiplication of a phase matrix and a material attribute matrix;
5) boundary setting: wherein boundary conditions are set according to different actual conditions; the boundary conditions can be periodic boundary conditions, fixed boundaries, adiabatic boundaries or mapping boundaries; in general, the inlet and the outlet of gas are fixed boundaries, and the contact boundary between a preform and a CVI furnace wall is an adiabatic boundary; for example, the periodic boundary condition is used for a small part of the whole large preform;
6) flow field calculation: wherein the LBM method is used to calculate the gas-phase flow field, and the standard Boltzmann equation in the form of BGK is $$f_i(r+v_i\Delta t, t+\Delta t) = f_i(r,t)(1-\omega) + \omega f_i^{eq}(r,t) + w_i S\Delta t,$$

where subscript i indicates direction; f is a distribution function; $f^{eq}$ represents the equilibrium distribution function; $\Delta t$ is the time step; V is the speed; r is the position; w is the collision frequency; $w_i$ is the direction-related weight factor; S is the reaction term calculated in step (7);
the core is divided into two sub-processes: a) taking a virtual time step so that all particles move without restriction on a set of virtual grids (that is, particles move in a free grid without considering boundary conditions); b) then, taking a modified time step, overlapping the phase matrix with the virtual grid in (a) according to the boundary conditions described by each phase matrix, and reflecting the gas-phase particles back to the gas-phase flow field according to the reflection boundary conditions to achieve the effect of modifying the flow field if the gas-phase particles enter the solid boundary;
7) chemical reaction calculation: wherein the chemical reaction is calculated by a phase transformation algorithm, which is to scale the chemical reaction according to the actual reaction relationship after calculation under specified conditions, and add and subtract on the basis of the phase matrix;
the amount of formation $R_i$ of the solid phase in the chemical reaction can be determined according to the reaction rate constant $ks_i$ and the gas-phase concentration C. In this algorithm, phase parameters $\Phi_i$ (given by a phase matrix) are introduced for modification, $R_i=\Phi_i ks_i C_i$; the calculated consumption of the solid phase is scaled according to the actual relationship $$P_i = \frac{R_i M_i \Delta t}{\rho_i},$$

where Mi is the molecular mass of the solid phase, and pi is the density of the solid phase i. Finally, adding and subtraction are performed on the phase matrix $\Phi_i(r,t+\Delta t)=\Phi_i(r,t)+:P_i$.

The value of the phase matrix is a solid matter, and the change of the value of the phase matrix is the densification process.

8) Circulating the steps 6) and 7) until the reaction ends;
9) processing results: wherein the calculated phase matrix is output and count, and is compared with the original matrix to obtain the relevant information after CVI densification.

Embodiments

Figure 3:
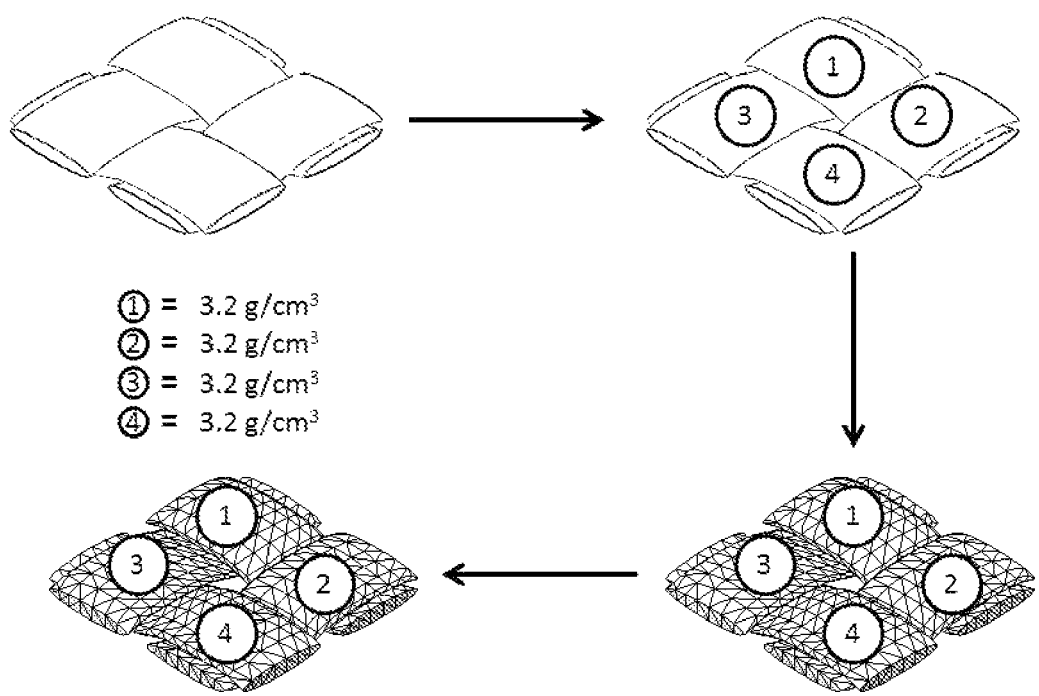
FIG. 3 is three-dimensional modeling, phase matrix, mesh division and material attribute assignment according to an embodiment of the present disclosure.

Geometric modelling: a three-dimensional model of a preform is made using SolidWorks® (CAD [@], Geodict®, etc.) software according to the actual preform construction, taking the two dimensional (2D) woven structure as an example, as shown in FIG. 3.

Assignment of a phase component: different phases are established based on different fiber numbers in the preform. According to the phase, any fiber can be distinguished. As shown in FIG. 3, each fiber can be identified by numbers 1, 2, 3 and 4.

Grid division: according to certain precision requirements, the model is divided by 270*270*32 grids.

Figure 4:
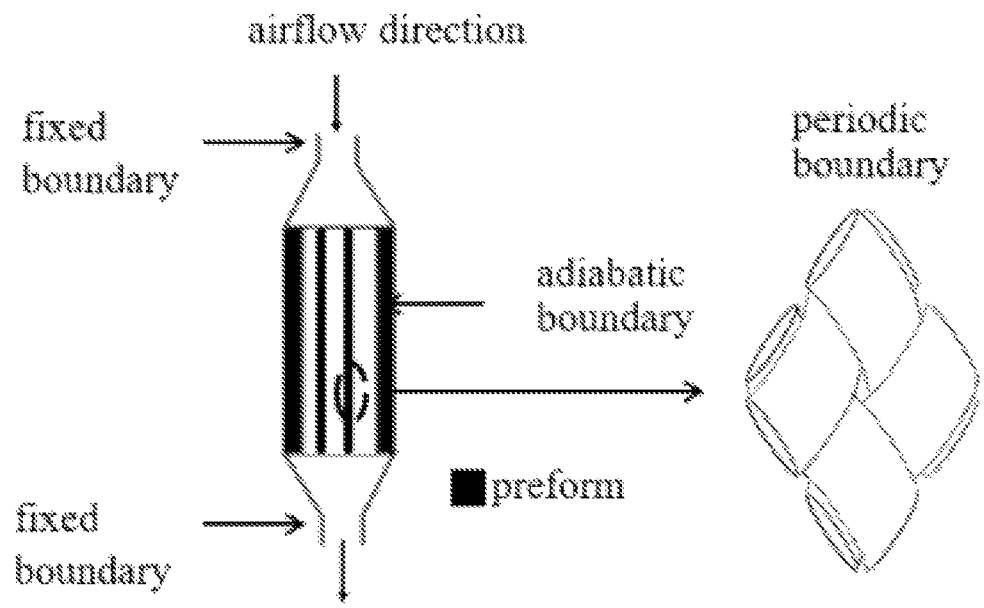
FIG. 4 is the boundary condition setting according to an embodiment of the present disclosure.

Assignment of material attributes: the material density is taken as the attribute input, and all fibers with different numbers are SiC fibers, to which a value is assigned at 3.2 g/cm3;

Boundary setting: boundary conditions are set according to different actual conditions. FIG. 4 is the boundary condition setting when the preform is deposited in a tubular furnace in the laboratory. Adiabatic boundary conditions are used at the boundary of the tubular furnace, which means that the gas cannot flow outward here. The internal structure of the preform may be periodically repeated, so that periodic boundary conditions are used, which means that repetition occurs along the sub-direction, thus saving the calculation cost.

Figure 5:
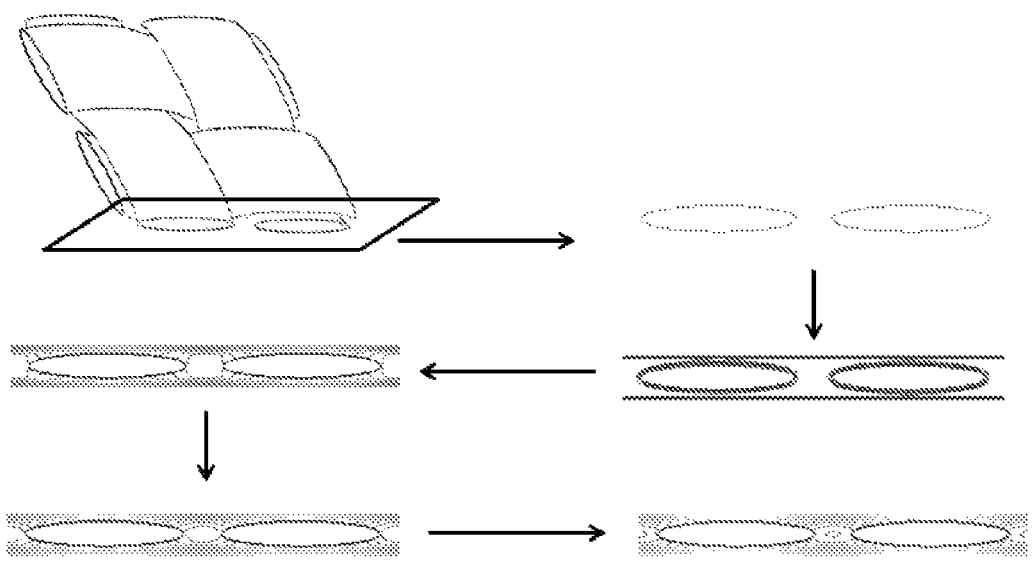
FIG. 5 is an evolution example of a flow field calculated by an LBM according to an embodiment of the present disclosure.

Flow field calculation: the LBM is used to calculate the gas-phase flow field. FIG. 5 shows the evolution of the flow field in the calculation process. The figure shows the contour line of gas substance concentration, and the introduction of gas results in the change of the concentration inside the preform. Initially, the gas does not meet the solid part of the preform, and the concentration is relatively uniform. With the introduction of gas, the blocking effect of the solid part of the preform becomes more and more obvious, forming an obvious concentration gradient. Finally, the time is long enough, and the concentration is uniform again in regions.

Figure 6:
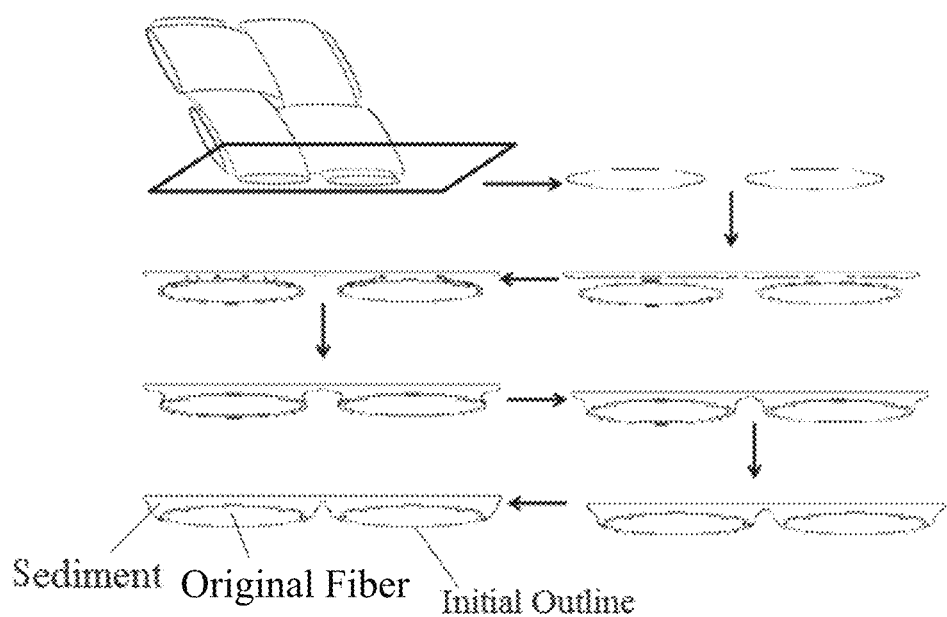
FIG. 6 is a demonstration diagram of the deposition process according to the embodiment of the present disclosure (white is a sediment and an original fiber, and black outline is an initial outline)

Chemical reaction calculation: the chemical reaction is calculated by a phase transformation algorithm. FIG. 6 shows the sedimentary evolution process. The figure shows the deposition of the target product inside the preform. After the gas is introduced, it contacts with the surface of the preform for reaction deposition, and deposition products are gradually accumulated. Finally, the ventilation inlet is completely closed and the ventilation is finished.

The steps 6) and 7) are circulated until the reaction ends. The end condition of the reaction is that the entrance of the boundary condition is completely closed, and the deposition process cannot continue.

Figure 7:
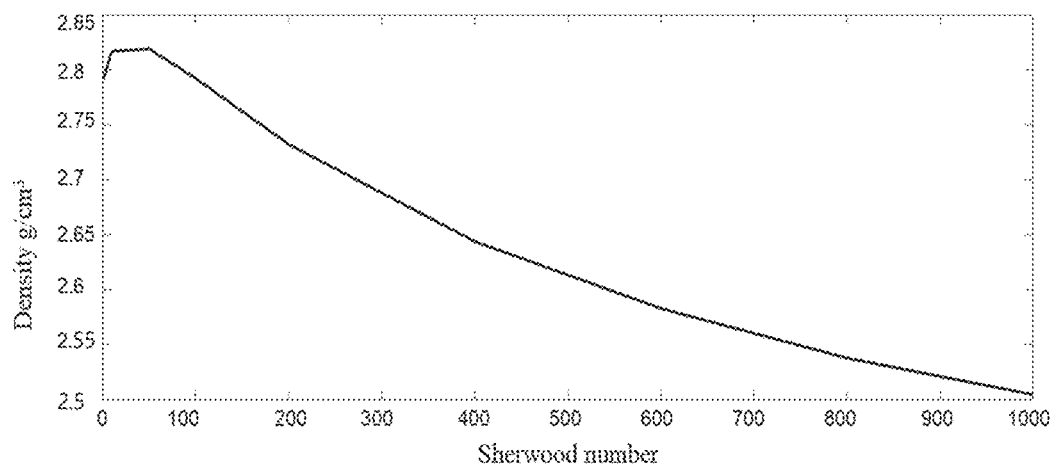
FIG. 7 is the final deposition density according to an embodiment of the present disclosure under different experimental conditions.

Processing results: the calculated phase matrix is output and count. Taking the density as an example, the sediment density is also 3.2 g/cm3, but due to the existence of pores in the space, the initial overall material density is obviously less than 3.2 g/cm3, and gradually approaches to 3.2 g/cm3 with the development of the deposition process. The final result is determined by the experimental conditions. FIG. 7 shows the results of density under different experimental conditions.

In the present disclosure, a specific example is applied to illustrate the principle and implementation of the present disclosure, and the explanation of the above embodiments is only used to help understand the method of the present disclosure and its core idea. At the same time, according to the idea of the present disclosure, there will be some changes in the specific implementation and application scope for those skilled in the art. To sum up, the contents of this specification should not be construed as limiting the present disclosure.

What is claimed:

1. A Boltzmann-based method for simulating a Chemical Vapor Infiltration (CVI) densification process of a composite material, comprising the steps of:
   a) modelling on a computer, a three-dimensional model of an actual preform, producing a three-dimensional matrix by scanning pixels one by one, recording a component number of each pixel at the same time, and storing component information of the pixel is in a matrix form in one-to-one correspondence with a spatial position, which is referred to as a component matrix;
   b) assigning a phase component: comprising extracting target attributes according to a spatial distribution relationship and attribute relationships recorded by the component matrix, establishing a matrix based on the target attributes, performing normalization processing to obtain a phase matrix, and counting volume occupancy of a certain phase in the spatial position from the phase matrix, wherein the volume occupancy is a ratio of an amount of substances in the phase component to an amount of all accommodated in space;
   c) dividing grid comprising re-dividing the phase matrix according to an actual precision requirement, and establishing an independent phase matrix for each of different phase components, wherein all the independent phase matrices are superimposed into a re-divided grid three-dimensional model of the actual preform;
   d) assigning material attributes comprising assigning material attributes according to a re-divided grid phase matrix by way of one-to-one multiplication of the independent phase matrix and the established matrix based on the target attributes;
   e) setting boundary conditions according to different actual conditions;
   f) calculating a gas-phase flow field by using a Lattice Boltzmann Method (LBM), comprising two sub-steps:
      1) Taking a virtual time step so that all particles move without restriction on a set of virtual grids; and 2) Then, taking a modified time step, releasing the particles entering the boundary according to the boundary conditions described by each independent phase matrix, and modifying the gas-phase flow field;
g) calculating a chemical reaction by a phase transformation algorithm, comprising scaling the chemical reaction according to an actual reaction relationship after calculation under specified conditions, and adding and subtracting on a basis of each independent phase matrix;
h) circulating the steps f) and g) until the reaction ends;
i) processing results-comprising outputting and counting calculated independent phase matrixes, and comparing each calculated independent phase matrix with an original matrix to obtain relevant information after CVI densification; and j) performing a CVI densification process on the actual preform according to the relevant information after CVI densification, and forming the composite material comprising the actual preform and a matrix.

2. The simulation method according to claim 1, wherein the boundary conditions in step e) can be periodic boundary conditions, fixed boundaries, adiabatic boundaries or mapping boundaries; wherein, boundaries between an inlet and an outlet of gas are fixed boundaries, and a contact boundary between a preform and a CVI furnace wall is an adiabatic boundary; the periodic boundary condition is for a small part of the preform.

3. The simulation method according to claim 1, wherein the three-dimensional model of the preform is drawn by computer design software.

\* \* \* \* \*